US012629198B2

(12) United States Patent
Batchelor et al.

(10) Patent No.: US 12,629,198 B2
(45) Date of Patent: May 19, 2026

(54) ANTI-STICK COATINGS INCLUDING FLUOROPHORES

(71) Applicant: GYRUS ACMI, INC., Westborough, MA (US)

(72) Inventors: Kester Julian Batchelor, Mound, MN (US); Teo Heng Jimmy Yang, Heath (GB); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 1131 days.

(21) Appl. No.: 17/651,115

(22) Filed: Feb. 15, 2022

(65) Prior Publication Data

US 2022/0257309 A1    Aug. 18, 2022

Related U.S. Application Data

(60) Provisional application No. 63/149,858, filed on Feb. 16, 2021, provisional application No. 63/201,325, filed on Apr. 23, 2021.

(51) Int. Cl.
| | |
|---|---|
| *A61B 18/14* | (2006.01) |
| *C09D 5/22* | (2006.01) |
| *C09D 7/63* | (2018.01) |
| *G01N 21/958* | (2006.01) |
| *A61B 17/00* | (2006.01) |
| *A61B 18/00* | (2006.01) |
| *G01N 21/84* | (2006.01) |

(52) U.S. Cl.
CPC ............ *A61B 18/1445* (2013.01); *C09D 5/22* (2013.01); *C09D 7/63* (2018.01); *G01N 21/958* (2013.01); *A61B 2017/00526* (2013.01); *A61B 2017/00902* (2013.01); *A61B 2017/00907* (2013.01); *A61B 2018/00077* (2013.01); *A61B 2018/00125* (2013.01); *A61B 2018/0013* (2013.01); *A61B 2018/00136* (2013.01); *A61B 2018/00148* (2013.01); *A61B 2018/0063* (2013.01); *G01N 2021/8427* (2013.01)

(58) Field of Classification Search
CPC .............. A61B 2018/0013; A61B 2018/00982
See application file for complete search history.

(56) References Cited

U.S. PATENT DOCUMENTS

| | | | | |
|---|---|---|---|---|
| 2017/0190139 A1* | 7/2017 | Haghdoost | ............... | B32B 3/18 |
| 2019/0090934 A1* | 3/2019 | Robinson | ........... | A61B 18/1206 |
| 2021/0307809 A1* | 10/2021 | Yorozu | ................. | C08G 77/20 |

FOREIGN PATENT DOCUMENTS

JP        2014087541 A  *  5/2014

* cited by examiner

*Primary Examiner* — Sean W Collins
(74) *Attorney, Agent, or Firm* — Schwegman Lundberg & Woessner, P.A.

(57) ABSTRACT

Various aspects of the present disclosure provide a medical device. The medical device includes a substrate. The medical device further includes a substantially transparent or translucent anti-stick coating disposed on a surface of the substrate. The anti-stick coating includes one or more fluorophores internally distributed in the anti-stick coating.

20 Claims, 6 Drawing Sheets

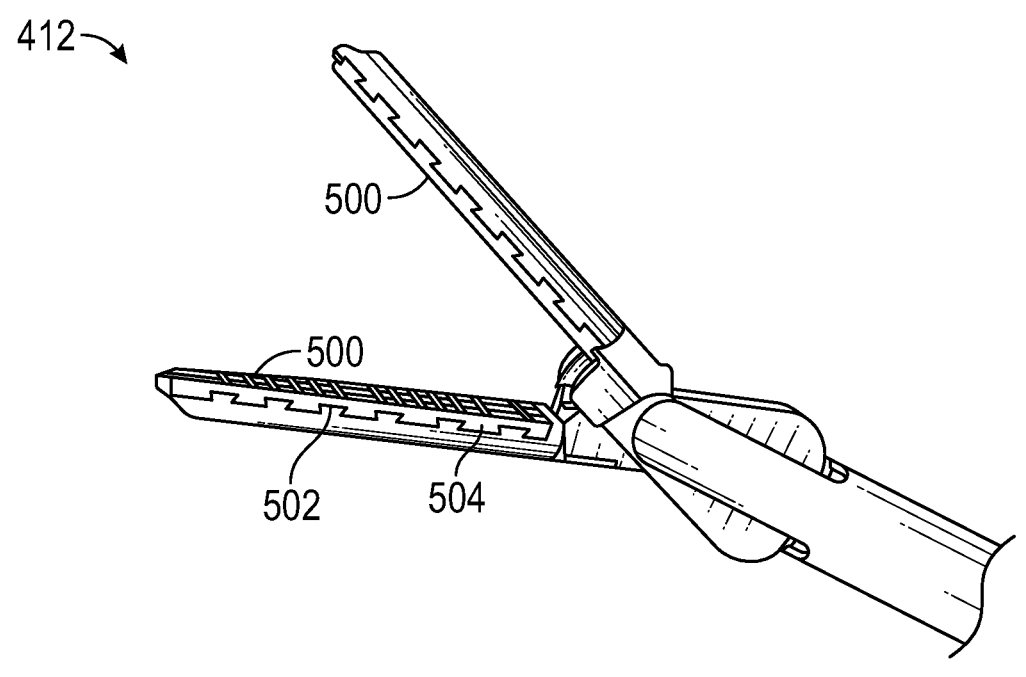

FIG. 5

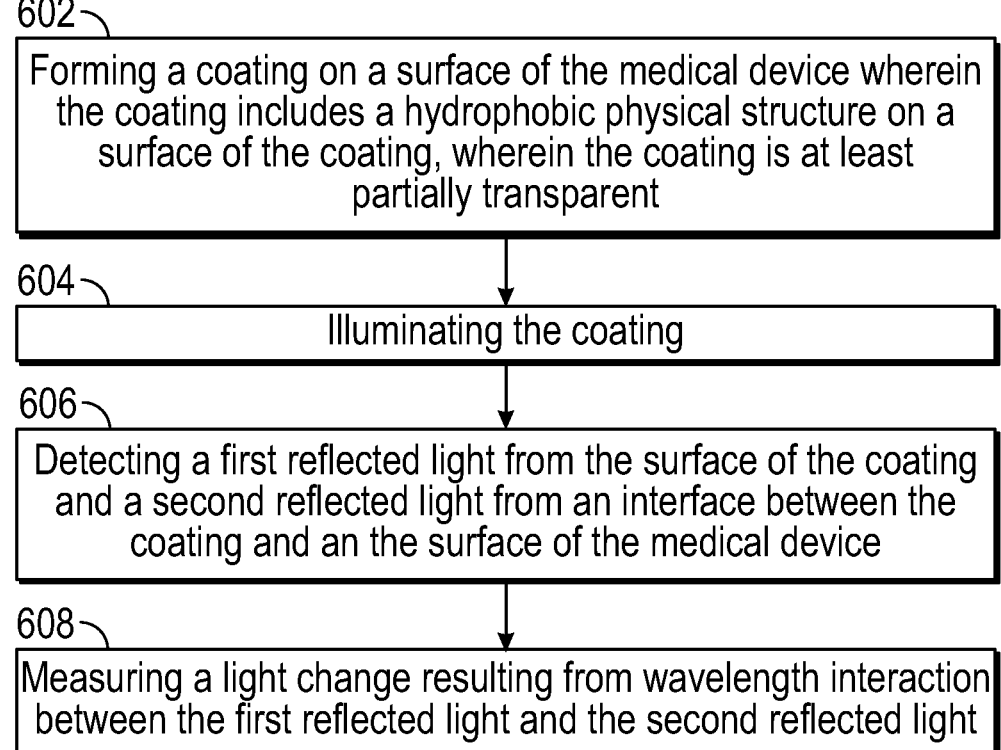

602
Forming a coating on a surface of the medical device wherein the coating includes a hydrophobic physical structure on a surface of the coating, wherein the coating is at least partially transparent 604
Illuminating the coating 606
Detecting a first reflected light from the surface of the coating and a second reflected light from an interface between the coating and an the surface of the medical device 608
Measuring a light change resulting from wavelength interaction between the first reflected light and the second reflected light

ANTI-STICK COATINGS INCLUDING FLUOROPHORES

CROSS REFERENCE TO RELATED APPLICATIONS

This application claims priority to U.S. Provisional Patent Application No. 63/149,858, titled "ANTI-STICK COAT-INGS INCLUDING FLUOROPHORES", filed on Feb. 16, 2021, the contents of which are hereby incorporated by reference. This application also claims priority to U.S. Provisional Patent Application No. 63/201,325, titled "INSPECTION DEVICE AND METHOD FOR COAT-INGS", filed on Apr. 23, 2021, the contents of which are hereby incorporated by reference.

SUMMARY OF THE INVENTION

Surfaces on medical devices or other industrial articles can be exposed to a wide variety of liquids. Accumulation of these liquids can cause significant damage or impair the operability of the device or article. It is, therefore, desirable to modify these devices or articles to mitigate the accumulation of liquids. However, detecting whether a coating is applied to a surface to help mitigate the accumulation of liquids can be difficult.

Various aspects of the present disclosure provide a medical device. The medical device includes a substrate. The medical device further includes a substantially transparent or translucent anti-stick coating disposed on a surface of the substrate. The anti-stick coating includes one or more fluorophores internally distributed in the anti-stick coating.

Various aspects of the present disclosure provide a method of making a medical device. The medical device includes a substrate. The medical device further includes a substantially transparent or translucent anti-stick coating disposed on a surface of the substrate. The anti-stick coating includes one or more fluorophores internally distributed in the anti-stick coating. The method includes disposing the anti-stick coating on at least a portion of the substrate.

Various aspects of the present disclosure provide a method of inspecting a medical device. The medical device includes a substrate. The medical device further includes a substantially transparent or translucent anti-stick coating disposed on a surface of the substrate. The anti-stick coating includes one or more fluorophores internally distributed in the anti-stick coating. The method includes contacting at least a portion of the medical device with electromagnetic radiation. The method further includes measuring a fluorescent emission from the medical device.

BRIEF DESCRIPTION OF THE FIGURES

The drawings illustrate generally, by way of example, but not by way of limitation, various aspects of the present invention.

FIG. 5 is a broken away perspective view of the jaws of the medical device of FIGS. 2A and 2B in the open position, in accordance with various aspects.

FIG. 6 shows a flow diagram of a method of manufacturing a device, in accordance with various aspects.

DETAILED DESCRIPTION OF THE INVENTION

Figure 1:
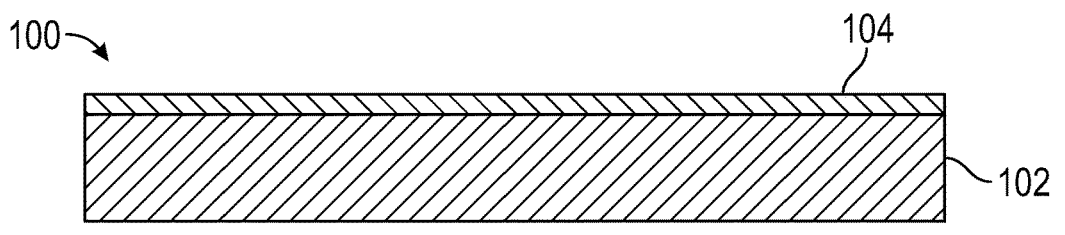
FIG. 1 is a sectional view of a portion of a medical device, in accordance with various aspects.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The polymers described herein can terminate in any suitable way. In some embodiments, the polymers can terminate with an end group that is independently chosen from a suitable polymerization initiator, —H, —OH, a substituted or unsubstituted $(C_1$-$C_{20})$hydrocarbyl (e.g., $(C_1$-$C_{10})$alkyl or $(C_6$-$C_{20})$aryl) interrupted with 0, 1, 2, or 3 groups independently selected from —O—, substituted or unsubstituted —NH—, and —S—, a poly(substituted or unsubstituted $(C_1$-$C_{20})$hydrocarbyloxy), and a poly(substituted or unsubstituted $(C_1$-$C_{20})$hydrocarbylamino).

FIG. 1 is a sectional view of medical device 100 that includes substrate 102 and anti-stick coating 104. Substrate 102 can be any portion of medical device (e.g., a jaw portion of medical device 100). Anti-stick coating 104 is disposed over at least a portion of substrate 102. For example, anti-stick coating 104 can be disposed over about 1% total surface area of substrate 102 to about 100% total surface area of substrate 102, about 5% total surface area of substrate 102 to about 95% total surface area of substrate 102, about 10% total surface area of substrate 102 to about 90% total surface area of substrate 102, about 15% total surface area of substrate 102 to about 85% total surface area of substrate 102, about 20% total surface area of substrate 102 to about 80% total surface area of substrate 102, about 25% total surface area of substrate 102 to about 75% total surface area of substrate 102, about 30% total surface area of substrate 102 to about 70% total surface area of substrate 102, about 35% total surface area of substrate 102 to about 65% total surface area of substrate 102, about 40% total surface area of substrate 102 to about 60% total surface area of substrate 102, about 45% total surface area of substrate 102 to about 65% total surface area of substrate 102, about 50% total surface area of substrate 102 to about 60% total surface area of substrate 102, or less than or equal to 100% total surface area of substrate 102 and greater than or equal to 1, 5, 10, 15, 20, 25, 30, 35, 40, 45, 50, 55, 60, 65, 70, 75, 80, 85, 90, or 95% total surface area of substrate 102. Anti-stick coating 104 can take the form of being a coating formed from the same material or mixture of materials as substrate 102 or at least the portion of substrate 102 to which anti-stick coating 104 is applied. In other examples, anti-stick coating 104 can be integral to substrate 102. In such an example, anti-stick coating 104 extends from substrate 102.

In aspects where anti-stick coating 104 is very thin, transparent, or translucent, it can be extremely difficult to quickly confirm that anti-stick coating 104 is applied to substrate 102. To address this difficulty, in some aspects, anti-stick coating 104 includes (e.g., is doped with) a fluorophore. Therefore, the medical device or a portion thereof, as shown in FIG. 1, can be exposed to electromagnetic radiation at a wavelength known to elicit a fluorescent emission from the fluorophore. If a fluorescent emission is observed, the presence of anti-stick coating 104 is visually confirmed.

Anti-stick coating 104 can be characterized by having a certain degree of hydrophobicity or oleophobicity. This can be helpful for medical devices, which are routinely exposed to a wide variety of biological fluids. Biological fluids can be water-based and include interstitial fluids, blood, and the like. Biological fluids can also include organic or oil based substances such as fatty tissue. Designing anti-stick coating 104 to have some degree of hydrophobicity or oleophobicity can help to reduce the degree to which biological fluids adhere to the medical device.

In some examples, anti-stick coating 104 can be characterized as being superhydrophobic or superoleophobic. As used herein, superhydrophobic (alternatively known as ultrahydrophobic) can refer to surfaces or portions of a surface that are highly hydrophobic (e.g., extremely difficult to wet). The contact angles of a water droplet on superhydrophobic material generally exceed 150°. This can be referred to as the "lotus effect," so named after the superhydrophobic leaves of the lotus plant. A droplet striking these kinds of surfaces can fully rebound like an elastic ball. Interactions of bouncing drops can be further reduced using special superhydrophobic surfaces that promote symmetry breaking, pancake bouncing or waterbowl bouncing. As used herein superoleophobic is a phenomenon where the contact angles of various oil droplets with low surface tension on a solid surface are larger than 150°.

Substrate 102 can be a flexible or a rigid structure. Substrate 102 can be substantially planar or non-planar. Examples of suitable non-planar substrates can include a curved substrate or an undulating substrate. In some examples, substrate 102 can have a planar portion along with a rounded portion, an undulating portion, or both. In some aspects, the portion of substrate 102 that is coated with anti-stick coating 104 can be a jaw or forceps portion of a medical device. The jaws or forceps can include a series of peaks and valleys. The peaks, valleys, or a combination thereof, can have anti-stick coating 104 applied thereto. Having anti-stick coating 104 doped with fluorophores in the peaks and valleys can be helpful because it can be very difficult to visually confirm whether anti-stick coating 104 is distributed over the peaks and valleys. It can also be difficult to test these areas of substrate 102 measuring a contact angle of a water-based or oil-based droplet. However, doping anti-stick coating 104 with a fluorophore is very helpful to provide a method to quickly provide visual indication that anti-stick coating 104 is present.

Substrate 102 can include any suitable material or combination of materials. For example, substrate 102 can include a metal, a plastic material, a ceramic, a glass, or a combination thereof. Suitable metals include iron, stainless steel, titanium, tantalum, platinum iridium, tungsten, copper, nickel, gold, aluminum, steel an alloy thereof, or a mixture thereof. Suitable plastic materials include a thermoplastic polymer a thermoset polymer, or a mixture thereof. Specific plastic materials can include a polyamide, a polycarbonate, a polyolefin, a polyester, a polyurethane, an epoxy, a copolymer thereof, or a mixture thereof. More specific plastics can include polytetrafluoroethylene, a styrene-butadiene copolymer, ethylene tetrafluoroethylene, a polyvinyl chloride, polyether urethane, a phenyl formaldehyde polymer, or a mixture thereof. Suitable examples of ceramics include yttria $(Y_2O_3)$, magnesia (MgO), aluminum oxide $(Al_2O_3)$, a magnesium aluminum oxide $(MgAl_2O_4)$, a carbide, an oxycarbide, a nitride, an oxynitride, a boride, an oxyboride, a sulfide, a selenide, a sulfo-selenide, silica, zirconia, silicon-carbide, silicon-nitride, aluminum nitride, or a mixture thereof. Suitable examples of glass include soda lime silicate glass, alkali aluminosilicate glass, alkali containing boro-silicate glass, alkali aluminophosphosilicate glass, alkali aluminoborosilicate glass, or a mixture thereof.

Anti-stick coating 104 can include a metal, a polymeric material, a ceramic, a glass, or a combination thereof. Suitable metals include iron, stainless steel, titanium, tanta-lum, platinum, iridium, tungsten, copper, nickel, gold, alu-minum, steel an alloy thereof, or a mixture thereof. Suitable polymeric materials include a thermoplastic polymer a ther-moset polymer, or a mixture thereof. Specific plastic mate-rials can include a polyamide, a polycarbonate, a polyolefin, a polyester, a polyurethane, an epoxy, a copolymer thereof, or a mixture thereof. More specific plastics can include polytetrafluoroethylene, a styrene-butadiene copolymer, eth-ylene tetrafluoroethylene, a polyvinyl chloride, polyether urethane, a phenyl formaldehyde polymer, or a mixture thereof. Suitable examples of glass include soda lime silicate glass, alkali aluminosilicate glass, alkali containing boro-silicate glass, alkali aluminophosphosilicate glass, alkali aluminoborosilicate glass, or a mixture thereof. Specific examples of materials for anti-stick coating 104 can include tungsten disulfide, hexamethyldisiloxane, tetramethyldisi-loxane, fluorosilane, polydimethysiloxane, a glass, a per-fluoropolyether, manganese oxide polystyrene, zinc oxide polystyrene, precipitated calcium carbonate, or a mixture thereof.

Where present, the superhydrophobic or superoleophobic properties of anti-stick coating 104 can be a result of anti-stick coating 104's structure. For example, anti-stick coating 104 can include a plurality of microstructures, a plurality of nanostructures, or a combination thereof. In various examples, the plurality of structural features are microstructures that independently have a major dimension in a range of from about 1 μm to about 1000 μm, about 250 μm to about 750 μm, about 400 μm to about 600 μm, less than, equal to, or greater than about 1 μm, 25, 50, 75, 100, 125, 150, 175, 200, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 μm. In various examples, the plurality of structural features are nanostructures and independently have a major dimension in a range of from about 1 nm to about 100 nm, about 10 nm to about 70 nm, about 30 nm to about 50 nm, less than, equal to, or greater than about 1 nm, 5, 10, 15, 20, 25, 30, 35, 40, 45, 50, 55, 60, 65, 70, 75, 80, 85, 90, 95, or about 100 nm. In various aspects a variable thickness of anti-stick coating 104 can result from imper-fections imparted during manufacturing.

Any microstructure or nanostructure can be a structural component of medical device 100. The microstructure or nanostructure can conform to any suitable shape. For example, an individual microstructure can be shaped as a microwire, a microrod, a microtube, a microsphere, or a microdroplet. In some examples, an individual nanostruc-ture can be shaped as a nanowire, a nanorod, a nanotube, a nanosphere, or a nanodroplet.

In examples that include a plurality of microstructures, a plurality of nanostructures, or a mixture thereof, a pitch between adjacent structural features can be constant across medical device 100. Alternatively, a pitch between adjacent structural features can be variable across medical device 100. In some examples, a pitch between adjacent structural features of a first plurality of structural features is constant and a pitch between adjacent structural features of a second plurality of structural features is variable. In some examples, the microstructures and the nanostructures can form a hier-archical structure in which the microstructures form a base structure and the nanostructures extend from the microstruc-tures. The hierarchical structure including the microstruc-tures and nanostructures can have a synergistic effect where the hydrophobicity, oleophobicity, or both is greater than that of a coating having only the microstructure or the nanostructure.

A thickness of anti-stick coating 104 can generally be in a range of from about 0.1 nm to about 300 nm, about 0.01 nm to about 15 nm, about 5 nm to about 10 nm, less than, equal to, or greater than about 0.1 nm, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 nm. In some examples, a thickness of anti-stick coating 104 is substantially constant across medical device 100. In some other examples, the thickness of anti-stick coating 104 is variable. In examples where the thickness of anti-stick coating 104 is variable across medical device 100, the thickness values described herein can be an average thickness value, a median thickness value, or representative of the major thickness value. A thickness of about 10 nm can provide a minimum level of non-stick performance and durability, and depending on the device and the number of intended uses, 20 nm may be more preferred. A thickness of about 300 nanometers can provide improved non-stick per-formance and durability over thinner coatings of the about 10-20 nm range. Above about 300 nanometers, additional performance and durability enhancements may not be real-ized, while additional cost is incurred. Further, depending on the particular device characteristics, coating thicknesses above 300 nm may undesirably affect electrical transmission from the tissue sealing plate to the tissue. Thus, in a possibly preferred example, the liquid phobic structure can include fluorosilane containing compounds less than the maximum of about 300 nanometers, such as having a thickness in a range from about 10 nanometers to about 200 nanometers, or more preferably in an range from about 20 nanometers to about 200 nanometers to provide the performance, durability and value.

Anti-stick coating 104 described herein can be continu-ously distributed about substrate 102. However, in some examples, anti-stick coating 104 can be discontinuously distributed about substrate 102. For example, the anti-stick coating 104 can be a first anti-stick coating 104 and medical device 100 can further include a second anti-stick coating adjacent to first anti-stick coating 104. In still further examples, anti-stick coating 104 can include any plural number of anti-stick coatings 104.

In examples that include multiple anti-stick coatings 104, the respective anti-stick coatings 104 can include the same material or combination of materials. Conversely, the respective anti-stick coatings 104 can include a different material or combination of materials. Additionally, the respective anti-stick coatings 104 can include identical microstructures, nanostructures, or combinations of micro-structures and nanostructures. However, in some examples, the respective anti-stick coatings 104 can include different microstructures, nanostructures, or combinations of micro-structures and nanostructures.

The material of anti-stick coating 104 can result in medical device 100 having a desired contact angle. The contact angle can be a measure of the average value of contact angles measured across medical device 100 or an absolute value thereof. Alternatively, the contact angle can be a measure of the average value of contact angles measured across anti-stick coating 104 or an absolute value thereof. According to various aspects, a contact angle can be at least 120 degrees, as determined using ASTM D7334-08, at least 130 degrees, at least 140 degrees, at least 150 degrees, at least 160 degrees, at least 170 degrees, at least 180 degrees in a range of from about 120 degrees to about 180 degrees, about 130 degrees to about 170 degrees, or about 140 degrees to about 160 degrees.

Although not shown, in some examples, an adhesive layer can be disposed between anti-stick coating 104 and substrate 102. Including an adhesive layer can be helpful in examples where anti-stick coating 104 and the substrate 102 include different materials or mixtures of materials. Examples of suitable adhesives in the adhesive layer can include a pressure-sensitive adhesive, an epoxy resin, or a mixture thereof. In some examples, adhesion can be enhanced by roughing or etching the portion of the substrate that contacts anti-stick coating 104, the portion of anti-stick coating 104 that contacts the substrate, or both. Roughing or etching can be accomplished using e-beam radiation, a chemical etchant (e.g., an acid), or a combination thereof.

Where present, the one more fluorophores are present in anti-stick coating 104 in any amount suitable to provide a visual fluorescent emission. For example, the one or more fluorophores can be present at less than about 10 wt % of anti-stick coating 104, less than about 5 wt % of anti-stick coating 104, or in a range of from about 0.1 wt % to about 10 wt % of anti-stick 104 coating or in a range of from about 2 wt % to about 4 wt % of anti-stick coating 104. The one or more fluorophores can be homogenously distributed about anti-stick coating 104. Alternatively, the one or more fluorophores are heterogeneously distributed about anti-stick coating 104. A homogenous distribution of the fluorophores can be helpful to confirm that anti-stick coating 104 is present across the entirety of anti-stick coating 104. A heterogenous distribution of the one or more fluorophores, however, can be helpful if the fluorophores are located within a portion of anti-stick coating 104 that is of particular interest and a user only wants to confirm that that anti-stick coating 104 is present at that location. Additionally, a heterogenous distribution of anti-stick coating 104, can save on costs since a smaller amount of fluorophore can be included compared to an amount of the one or more fluorophores required to provide a homogenous distribution of the one or more fluorophores.

The one or more fluorophores of anti-stick coating 104 can include the same fluorophore disposed therein. Alternatively, anti-stick coating 104 can include different fluorophores. The degree of similarity between fluorophores can relate to their chemical composition, the wavelength or range of wavelengths of electromagnetic radiation the fluorophore absorbs, the wavelength or range of wavelengths of electromagnetic radiation the fluorophore emits, or both.

Including different fluorophores can be beneficial for various non-limiting reasons. For example, if medical device 100 includes different anti-stick coatings 104 (e.g., different compositions) each anti-stick coating 104 can have a respective different fluorophore. The different fluorophores, for example, can emit electromagnetic radiation having different wavelengths. Therefore, the presence of the different anti-stick coatings 104 can be confirmed. Referring to the hierarchical structures described herein, the material of the microstructure can have a first fluorophore disposed therein and the material of the nanostructure can have a second fluorophore that emits electromagnetic radiation at a different wavelength than the first fluorophore. Therefore, if electromagnetic radiation of the first fluorophore and second fluorophore is observed, the presence of the microstructure and nanostructure is confirmed.

In some other examples, if anti-stick coating 104 is disposed on substrate 102 in a plurality of stacked layers, each layer of anti-stick coating 104 can have a different fluorophore distributed therein. Therefore, the presence of each layer of anti-stick coating 104 can be confirmed by observing the electromagnetic radiation associated with each fluorophore in their respective layer.

The fluorophores can also help to determine the thickness of anti-stick layer 104. For example, if anti-stick layer 104 includes a homogeneous distribution of fluorophores, the electromagnetic emissions from the fluorophores can be quantified and associated with their respective locations along the thickness of anti-stick layer 104. Alternatively, X-ray fluorescence can be used to determine the respective locations of the fluorophores along the thickness of anti-stick layer 104.

There are a wide array of fluorophores that can be used in association with anti-stick coating 104. Although the one or more fluorophores are generally disposed within anti-stick coating 104 (e.g., the exterior surface of anti-stick coating is free of the one or more fluorophores), it can be desirable for the fluorophores to be biocompatible. Biocompatibility is generally understood to relate to a material possessing the quality of being free of toxic or injurious effects on biological systems. If the fluorophores are biocompatible, they can be disposed on the exterior of anti-stick coating 104. Additionally, if the fluorophores are biocompatible it can mitigate harm caused by exposing the fluorophores to the body if anti-stick coating 104 is damaged or an interior of anti-stick coating 104 is exposed.

The fluorophores that can be included in anti-stick coating 104 can include an organic non-protein fluorophore, an organic dye, a nucleic acid dye, a fluorescent protein, or a mixture thereof. Examples of organic non-protein fluorophores include xanthene, cyanine, squaranine, squarine rotaxane, naphthalene, coumarin, oxadiazole, anthracene, pyrene, oxazine, acridine, arylmethine, tetrapyrrole, dipyrromethene, a derivative of any one of the preceding, or a mixture thereof. Examples of organic dyes include hydroxycoumarin, aminocoumarine, methoxycoumarine, allophycocyanin, or a mixture thereof. Examples of nucleic acid dyes include 4',6-diamidino-2-phenylindole, plicamycin, toyomycin, ethidium bromide, propidium iodide, or a combination thereof. An example of a fluorescent protein include a green fluorescent protein.

Figure 2:
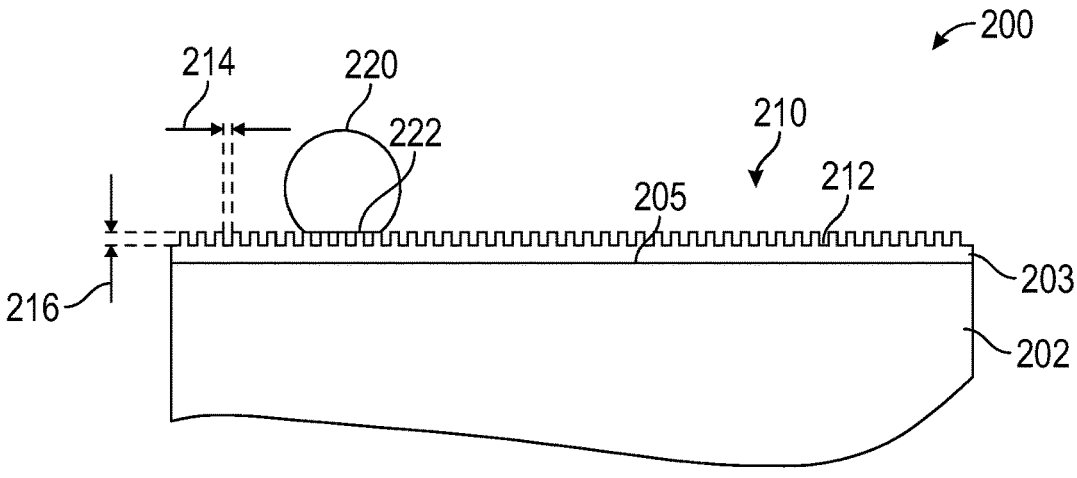
FIG. 2 shows a surface with a hydrophobic physical structure, in accordance with various aspects.

FIG. 2 shows one example of a surface with a hydrophobic physical structure 210, akin to anti-stick coating 104 disposed on a coating 203 of a substrate 202. The substrate 202 can be a medical device such as medical device 100. The hydrophobic physical structure 210 may be on all or a portion of a surface, and different hydrophobic physical structures 210 may be used on different surfaces or components of a medical device.

As shown in FIG. 2, in one example, the hydrophobic physical structure 210 includes asperities 212 having a height 216 and a pitch 214. The hydrophobic physical structure 210 can be described by the following equation:

$$\Lambda_C = \frac{-\rho g V^{1/3}\left(\left(\frac{1-\cos(\theta_a)}{\sin(\theta_a)}\right)\left(3+\left(\frac{1-\cos(\theta_a)}{\sin(\theta_a)}\right)^2\right)\right)^{2/3}}{(36\pi)^{1/3}\gamma\cos(\theta_{a,0}+w-90)}$$

where $\Lambda$ is a contact line density, and $\Lambda_c$ is a critical contact line density; $\rho$=density of the liquid droplet; g=acceleration due to gravity; V=volume of the liquid droplet; $\theta_a$=advancing apparent contact angle; $\theta_{a,o}$=advancing contact angle of a smooth substrate; $\gamma$=surface tension of the liquid; and w=tower wall angle.

The contact line density $\Lambda$ is defined as a total perimeter of asperities over a given unit area.

In one example, if $\Lambda > \Lambda_c$ then a droplet 220 of liquid are suspended in a Cassie-Baxter state. Otherwise, the droplet 220 will collapse into a Wenzel state. In one example when a Cassie-Baxter state is formed, an ultra-hydrophobic condition exists, and a low adhesion surface is formed. FIG. 2 illustrates a Cassie-Baxter state, where the droplet 220 rests on top of the asperities 212 at interface 222. Although rectangular asperities are shown for illustration purposes, the disclosure is not so limited. Asperity shapes are taken into account in the formula above, at least in the tower wall angle (w) term.

One method of forming asperities includes chemical etching. Another example of forming asperities includes laser etching or ablation. Another example of forming asperities includes ion etching. In the example of FIG. 2, the hydrophobic physical structure 210 is formed as part of a coating 203 that forms a direct interface 205 with substrate 202.

In one example, the asperities 212 are formed by application of nanoparticles to a surface of the substrate 202 to form the coating 203. In one example, the asperities 212 are formed by application of a continuous coating that assembles to form a nanoscale physical structure on a surface of the coating 203. In one example, the asperities 212 are formed by application of nanoparticles to a surface of the coating 203. In one example, the nanoparticles include a polysiloxane. In one example, the nanoparticles include hexamethyldisiloxane (HMDSO) particles. In one example, the nanoparticles include tetramethyldisiloxane (TMDSO) particles. In one example, the nanoparticles include fluorosilane particles. Other nanoparticle materials are also within the scope of the invention. In one example, a hydrophobic chemistry of the nanoparticle, in combination with a nano scale asperity structure as shown in FIG. 2 provide better hydrophobicity compared to a hydrophobic chemistry alone.

Figure 3:
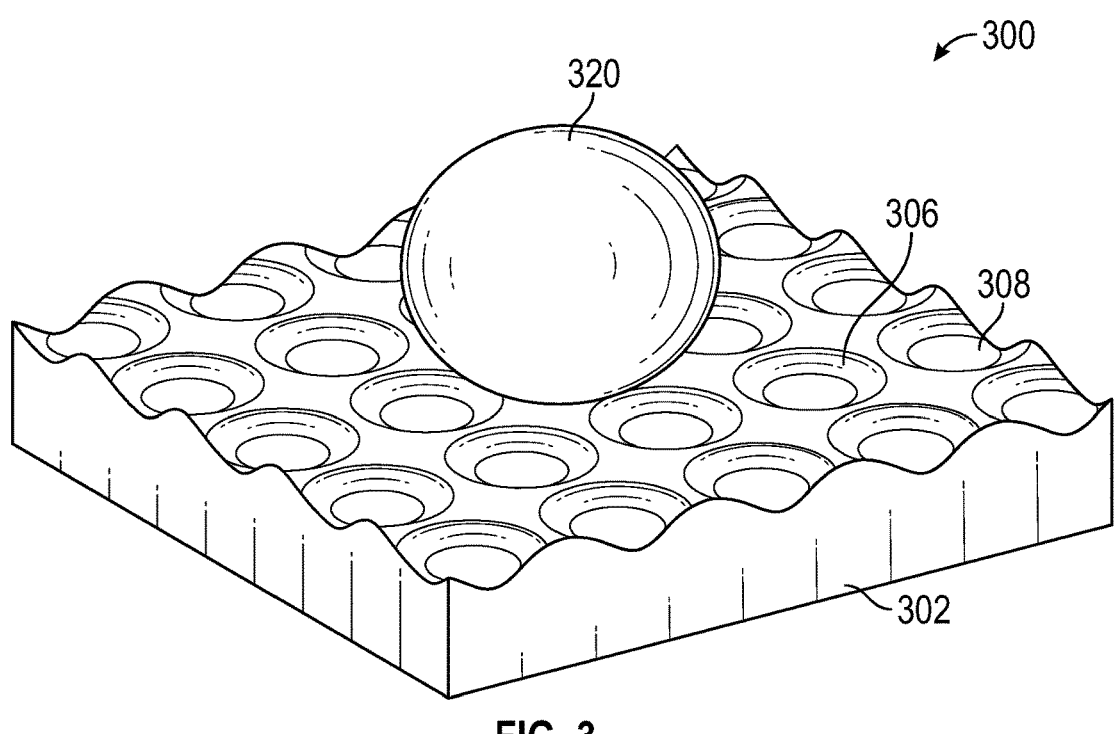
FIG. 3 shows a laser etched surface that includes hydrophobic physical structure

FIG. 3 shows one example of a laser etched surface 300 that includes hydrophobic physical structure as described above with respect to FIG. 2. In the example of FIG. 3, a gaussian hole array is formed by applying laser energy to a surface of a coating 302 in a controlled regular pattern to form holes 306. A shape of the holes 306 is characterized as gaussian due to the energy distribution of laser energy in forming the array. In the example shown, a number of asperities 308 are formed in the process that may be spaced and arranged in an array that provides a Cassie-Baxter state as described above. A liquid droplet 220 is illustrated on the hydrophobic physical structure similar to the droplet 220 from FIG. 2.

Medical device 100 or any medical device referred to can be one of many types of medical devices. For example, suitable medical devices can include a cauterizer, forceps, a ventilator, a pacemaker, a stent, a catheter, a hearing aid, a prosthesis, a joint replacement, a mesh, a staple, a guide wire, an endoscope, or a combination thereof. For illustrative purposes only, an example of medical device 100 as a forceps device is described below.

Figure 4A:
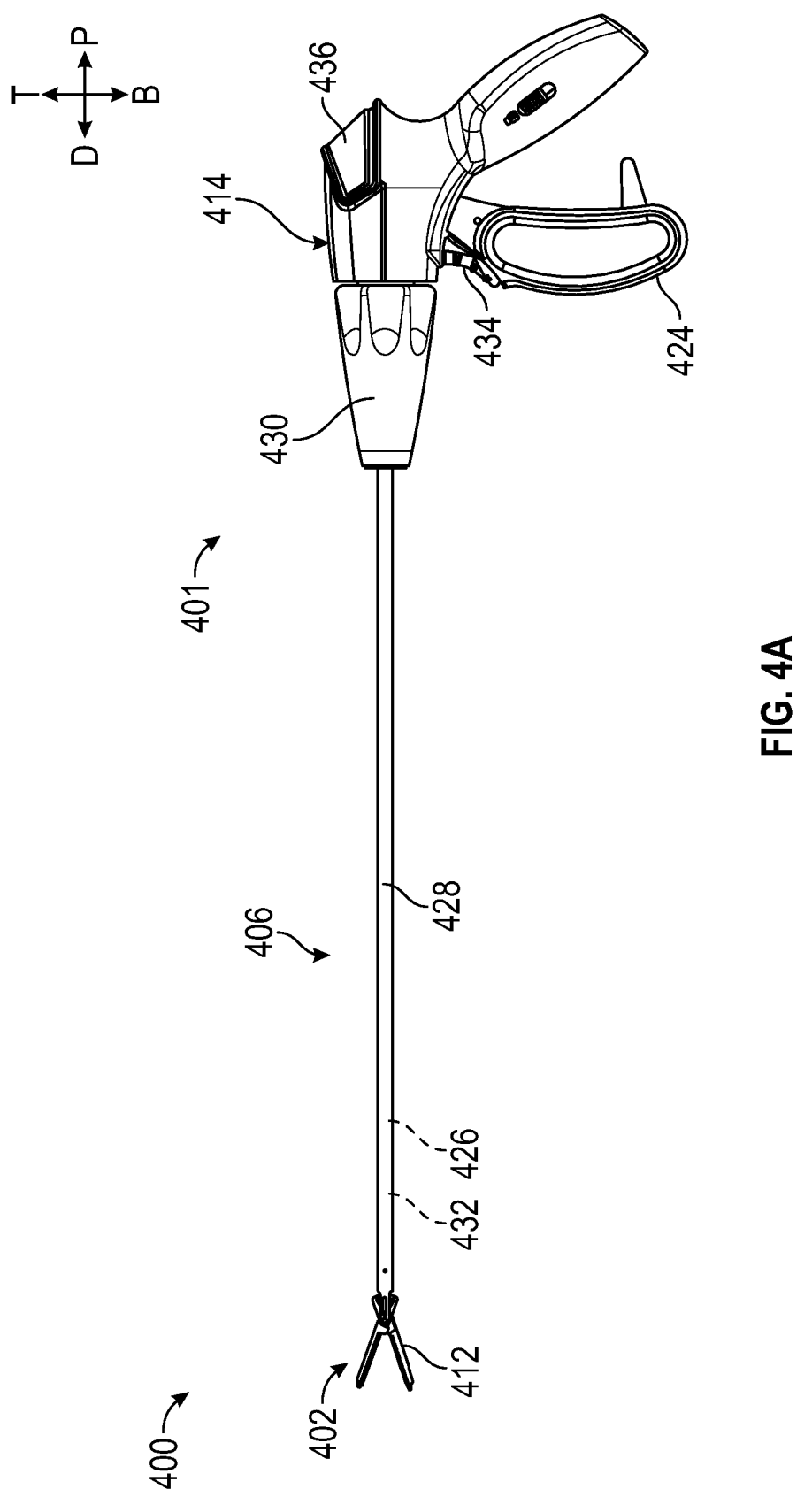
FIG. 4A is a side view of a forceps medical device including jaws in a closed position, in accordance with various aspects.
Figure 4B:
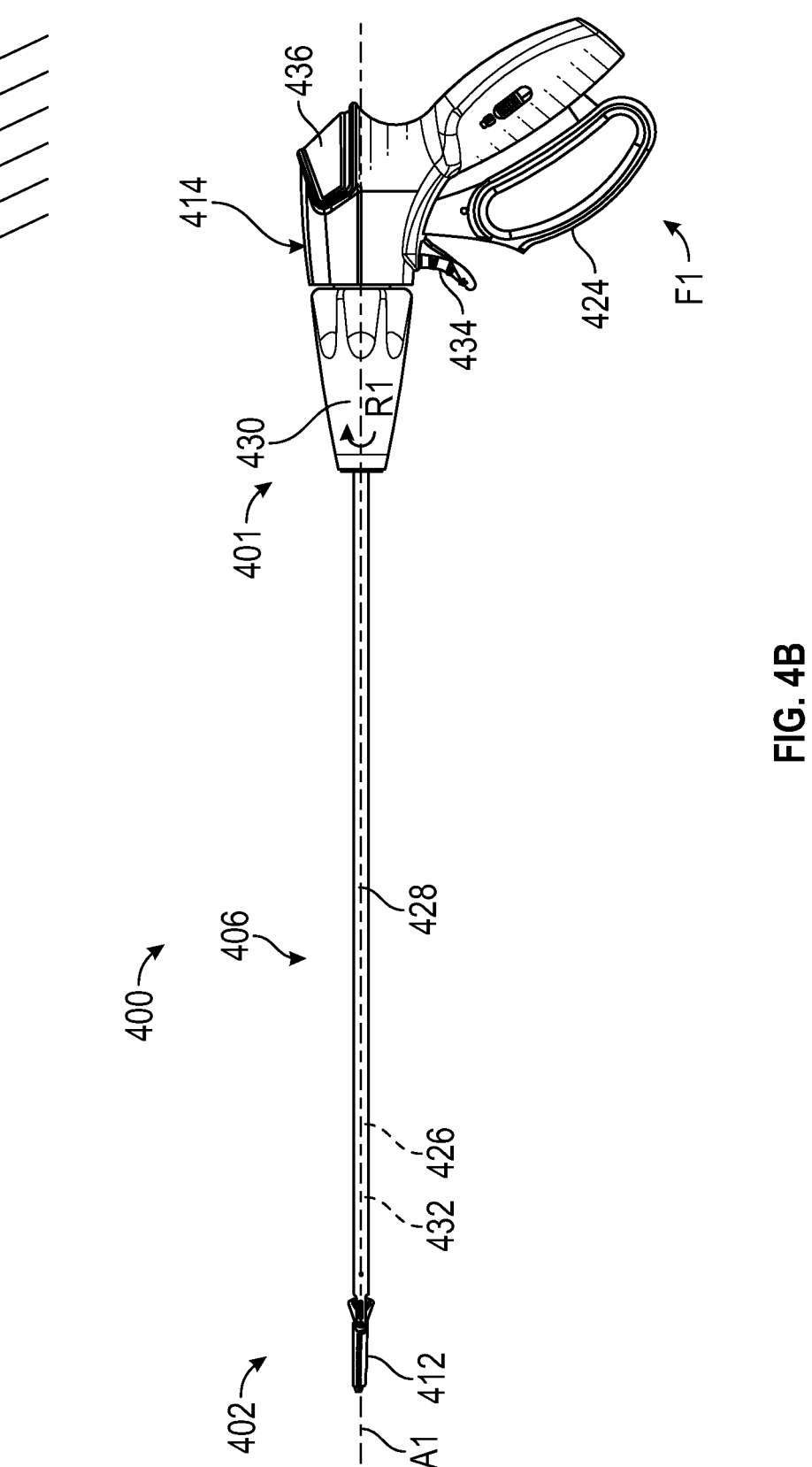
FIG. 4B is a side view of the forceps medical device of FIG. 2A including jaws in an open position, in accordance with various aspects.

FIG. 4A illustrates a side view of forceps 400 with jaws 412 in an open position. FIG. 4B illustrates a side view of forceps 400 with jaws 412 in a closed position. Directional descriptors such as proximal and distal are used within their ordinary meaning in the art. The proximal direction P and distal direction D are indicated on the axis provided in FIG. 4A. Opposite to the lateral directions L and L', is the medial direction, in other words, the medial direction is towards the centerline, or longitudinal axis A1 of forceps 400 (FIG. 4B).

The illustrative forceps 400 can include handpiece 401 at a proximal end, and end effector 402 at a distal end. An intermediate portion 406 can extend between handpiece 401 and end effector 402 to operably couple handpiece 401 to end effector 402. Various movements of end effector 402 can be controlled by one or more actuation systems of handpiece 401. In the illustrative example, end effector 402 can include jaws 412 that are capable of opening and closing. The end effector 402 can be rotated along a longitudinal axis A1 (FIG. 4B) of forceps 400. The end effector 402 can include cutting blade and an electrode for applying electromagnetic energy. All actuation system functions and all end effector actions are not required in all examples. The functions described herein can be provided in any combination.

An overview of features of forceps 400 is provided in FIGS. 4A and 4B. As shown broadly in FIGS. 4A and 4B, forceps 400 can include jaws 412, housing 414, lever 424, drive shaft 426, outer shaft 428, rotational actuator 430, blade assembly, trigger 434 and activation button 436. In this example, end effector 402, or a portion of end effector 402, such as jaws 412 can be one or more of: opened, closed, and rotated. In some examples, end effector 402, such as blade 432A of end effector 402, can be extended or retracted, and jaws 412 can be electromagnetically energized (e.g., electrically energized). In some examples, the energy can be radio-frequency energy.

To operate end effector 402, the user can displace lever 424 proximally by applying an input force F1 (FIG. 4B) to drive jaws 412 from the open position (FIG. 4A) to the closed position (FIG. 4B). In the example of forceps 400, moving jaws 412 from the open position to the closed position allows a user to clamp down on and compress a tissue. The handpiece 401 can also allow a user to rotate end effector 402. For example, rotating rotational actuator 430 (e.g., a user applying a rotational input R1, FIG. 4B) causes end effector 402 to rotate by rotating both drive shaft 426 and outer shaft 428 together.

In some examples, with the tissue compressed between jaws 412, a user can depress activation button 436 to cause an electrical energy, such as an electromagnetic energy, to be delivered to end effector 402, such as to an electrode of jaws 412. Application of electromagnetic energy can be used to seal or otherwise affect the tissue being clamped. In some examples, the electromagnetic energy can cause tissue to be coagulated, cauterized, sealed, ablated, desiccated or can cause controlled necrosis.

The handpiece 401 can enable a user to extend and retract blade 432A attached to a distal end of blade shaft 432. The blade 432A can be extended by displacing trigger 434 proximally. The blade 432A can be retracted by allowing trigger 434 to return distally to a default position. The default position of trigger 434 is shown in FIG. 4A. In some examples, as described herein, handpiece 401 can include features that inhibit blade 432A from being extended until jaws 412 are at least partially closed, or fully closed.

The forceps 400 can be used to perform a treatment on a patient, such as a surgical procedure. In an example, a distal portion of forceps 400, including jaws 412, can be inserted into a body of a patient, such as through an incision or another anatomical feature of the patient's body. While a proximal portion of forceps 400, including housing 414 remains outside the incision or another anatomical feature of the body. Actuation of lever 424 causes jaws 412 to clamp onto a tissue. The rotational actuator 430 can be rotated via a user input to rotate jaws 412 for maneuvering jaws 412 at any time during the procedure. Activation button 436 can be actuated to provide electrical energy to jaws 412 to coagulate, cauterize or seal the tissue within closed jaws 412. Trigger 434 can be moved to translate blade 432A distally to cut the tissue within jaws 412.

In some examples, forceps 400, or other medical device, may not include all the features described or may include additional features and functions, and the operations may be performed in any order. The handpiece 401 can be used with a variety of other end effectors to perform other methods.

FIG. 5 is a broken away view of jaws 412 of FIGS. 4A and 4B. As shown, jaws include textured surface 500. Textured surface 500 generally has an undulating profile defined by a series of peaks 502 and valleys 504. Textured surface 500 can increase jaw 412's grip on a tissue or aid in cutting, where desired. Anti-stick coating 104 can be applied at least to textured surface 500. This can help to reduce the degree to which biological tissues, biological fluids, or the like are adhered to jaws 502. Additionally, it can be very difficult to confirm whether an anti-stick coating is successfully applied to peaks 502 and valleys 504 using tests such as contacting peaks 502 and valleys 504 with a fluid and measuring the contact angle. However, including the one or more fluorophores in anti-stick coating 104 can allow a user to quickly receive a visual indication that anti-stick coating is applied to the portions of peaks 502 and valleys 504 that are desired.

Beyond keeping a griping or cutting surface of jaw 402, free of a biological fluid or tissue, anti-stick coating 104 can be beneficially applied to other features of medical device 100. For example, anti-stick coating 104 be disposed on a button, a trigger, a graphical user interface, a visual indicia (e.g., a word, a number, a pattern, a picture, a color, or a combination thereof), or a combination thereof. Without anti-stick coating 104, the biological fluid may obscure a visual indicia or graphical user interface. Obscuring either of these could make it difficult for a user (e.g., physician) to read and understand the visual indicia. This can be problematic, for example, if the visual indicia indicates that a certain button engages, for example, a cutting feature, a cauterizing feature, or any other feature. Obscuring a graphical user interface can be problematic if a medical device uses the graphical user interface to deliver instructions to the user. Additionally, obscuring a graphical user interface can be problematic if the graphical user interface displays touch buttons to activate certain functions. Additionally, obscuring a trigger of a medical device can have many of the same drawbacks as mentioned herein with respect to buttons, with the addition that allowing a biological fluid to accumulate on a button or trigger can result in a slippery surface. A slippery surface on the button or trigger can make it difficult to press or pull the button or trigger as well as increase the risk of inadvertently pressing or pulling the button or trigger. In some examples, medical device 100 can include a haptic feature that allows a user to navigate the device by feeling the haptic features. Obscuring the haptic feature with a biological fluid, may make it difficult to feel the haptic feature correctly.

Including anti-stick coating 104, or any other coating mentioned herein, can help to address these drawbacks by providing a surface that mitigates the accumulation of the biological fluid thereon. In some examples, anti-stick coating 104 can be substantially transparent. If anti-stick coating 104 is substantially transparent, anti-stick coating 104 can be advantageously disposed over a visual indicia or graphical user interface so that the features thereof are substantially unobscured by anti-stick coating 104. In some examples, anti-stick coating 104 can include metal particles to allow anti-stick coating 104 to be electrically conductive, which can be helpful if anti-stick coating 104 is disposed over a graphical user interface that is a touch screen. Suitable metal particles include gold, silver, copper, alloys thereof, or combinations thereof.

Medical device 100 can be manufactured according to many suitable methods. As an example of a suitable method, anti-stick coating 104 can be disposed over at least a portion of substrate 102. Examples of suitable disposing techniques include a sol-gel coating process, a cold spray coating process, chemical vapor deposition, physical vapor deposition, a thermal spray deposition, an in situ polymerization (e.g., plasma polymerization), a spin-coating deposition, a dip-coating deposition, an electrodeposition, additive manufacturing, or a combination thereof. The one or more fluorophores can be mixed with the anti-stick coating material before anti-stick coating 104 is applied to substrate 102. Structural features of anti-stick coating 104 such as nanofeatures, microfeatures, or both as described above, can be formed during the disposing step. Alternatively, the nanofeatures, microfeatures, or both can be formed in an additional step such as molding, imprinting, etching, or a combination thereof, to impart the structural microstructure feature, structural nanostructure feature, or a combination thereof.

FIG. 6 shows a flow diagram of another method of manufacture according to one example. In operation 602, a coating is formed on a surface of the medical device wherein the coating includes a hydrophobic physical structure on a surface of the coating, wherein the coating is at least partially transparent. In operation 604, the coating is illuminated. In operation 606, a first reflected light from the surface of the coating and a second reflected light from an interface between the coating and the surface of the medical device are detected. In operation 608, a light change is measured resulting from wavelength interaction between the first reflected light and the second reflected light.

Regarding operation 602, several modification/application techniques may be used to form the hydrophobic physical structure. Different coating methods outlined below may have varying ability to control coating integrity. It can be advantageous to be able to measure and quantify different coatings as described above.

In one example, a sol-gel process is used. Advantages of sol-gel application include the ability to coat more complex surfaces with high quality films. Challenges of sol-gel may include brittleness, limited thickness options, and induced mechanical stresses in the coating.

In one example, a cold spray process is used. Advantages of cold spray application include the ability to coat at lower temperatures, with low deterioration, low oxidation, and low defects. Challenges of cold spray may include high energy needed for application, high cost, and a limited number of compatible substrates.

In one example, a chemical vapor deposition (CVD) process is used. Advantages of CVD application include a high quality coating, high control of thickness, and the ability to coat complex surfaces. Challenges of CVD may include high temperature requirements, and high cost.

In one example, a physical vapor deposition (PVD) process is used. Advantages of PVD application include the ability to coat inorganic compounds, ecological friendly processes, and a wide variety of available coating materials. Challenges of PVD may include high vacuum chamber requirements and high cost.

In one example, a thermal spray process is used. Advantages of thermal spray application include a large selection of compatible coating materials and substrate materials, and low cost. Challenges of thermal spray may include difficulty in forming thick coatings, low adhesion issues of coatings, and ecologically unfriendly process steps.

In one example, an in-situ polymerization process is used. Advantages of in-situ polymerization include the ability to coat with insoluble polymers. Challenges of in-situ polymerization may include process complexity, high cost, and limited potential for large scale production.

In one example, a spin coating process is used. Advantages of spin coating include high quality coatings, fast drying times, and controllable thicknesses. Challenges of spin coating may include difficulty coating small surfaces and requirements of a smooth surface.

In one example, a dip coating process is used. Advantages of dip coating include the ability to coat complex surfaces and the ability for large scale production. Challenges of dip coating may include undesirable solvent requirements, and limitations of only soluble polymer coatings.

In one example, an electrodeposition process is used. Advantages of electrodeposition include high quality coatings at low cost. Challenges of electrodeposition may include long process times, and conductive substrate requirements.

Although a number of examples of coating processes are provided for forming hydrophobic physical structures, the invention is not so limited. Other processes that result in hydrophobic physical structures are also within the scope of the invention. It is also noted that coatings formed by the processes described above will result in physical differences, such as microstructures or nanostructures, interface characteristics, etc. that are detectable to one of ordinary skill in the art in a final product upon inspection. As such one of ordinary skill in the art will be able to discern which technique was used to form the hydrophobic physical structures by examining the final product.

In one example, application of appropriately sized and spaced nanoparticles using any one or more of the methods described above provides the desired structure of asperities. In one example, a coating may be etched as described above to create all or a part of the desired structure of asperities.

Figure 7:
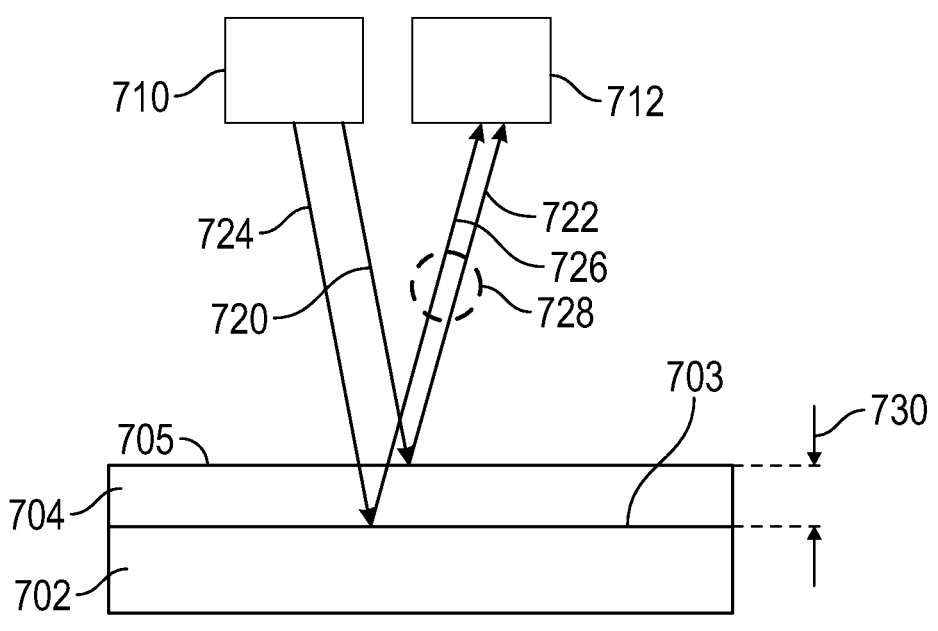
FIG. 7 schematically illustrates a method of inspecting a coating on a medical device, in accordance with various aspects.

In some aspects the hydrophobic coating might not include a fluorophore. FIG. 7 illustrates a method of inspecting a coating on a medical device which may not include a fluorophore, although the method can also be used to inspect a coating that does include a fluorophore. A portion of a medical device 702 is shown with a coating 704. An interface is formed between the coating 704 and a surface 703 of the medical device. In one example, the coating is at least partially transparent to allow at least some fraction of light to pass through the coating to the surface 703 of the medical device and reflect back out again.

FIG. 7 further shows a light source 710 and a reflected light detector 712. The term light source may refer to any of a number of energy beams that propagate in a wave. Light emitted from the light source may be in the visible light range, however the invention is not so limited. In one example, the light source 710 emits ultraviolet light. In one example the light source 1710 emits polychromatic light, such as white light, which is composed of a number of different colors (wavelengths). Although white light is used as an example, other combinations of wavelengths in polychromatic light are also within the scope of the invention. In one example the light source 710 emits monochromatic light. An example of monochromatic light may include blue light (around 500 nm wavelength) or any other single wavelength of light.

For illustration purposes, the light source 710 emits a first source beam 720 that reflects off a surface 705 of the coating 704 in a first reflected light beam 722. The light source 710 also emits a second source beam 725 that reflects off the surface 703 of the medical device 702 in a second reflected light beam 726. Due to the thickness 730 of the coating 704, there is a travel distance that is different between the first reflected light beam 722 and the second reflected light beam 726. The difference will cause wavelength interaction along the return path region 728 between the first reflected light and the second reflected light. In one example, the wavelength interaction is constructive interference. In one example, the wavelength interaction is destructive interference. The type and magnitude of interaction will depend on factors of the coating, including, but not limited to, thickness, transmittance, index of refraction, etc.

In one example, the wavelength interaction includes a color shift that is detectable by the reflected light detector 712. In one example the wavelength interaction may also be detectable by the naked eye, although the disclosure is not so limited. For example, with a polychromatic light source, such as white light, if a blue wavelength of light experiences constructive interference, the color may shift to a bluer color. Conversely, with a polychromatic light source, such as white light, if a blue wavelength of light experiences destructive interference, the color may shift to a less blue color. Although blue is used as an example, the invention is not so limited. A color or wavelength chosen for an indicator will depend on factors discussed above, such as thickness, transmittance, index of refraction, etc. of the coating being inspected.

In one example, the wavelength interaction includes an attenuation or decrease in intensity that is detectable by the reflected light detector 712. In one example the wavelength interaction may also be detectable by the naked eye, although the invention is not so limited. For example, with a monochromatic light source tailored to an expected thickness of coating, destructive interference can be used to detect the coating by observing or measuring a decrease in intensity. Constructive interference can also be used to detect the coating by observing or measuring an increase in intensity.

Figure 8:
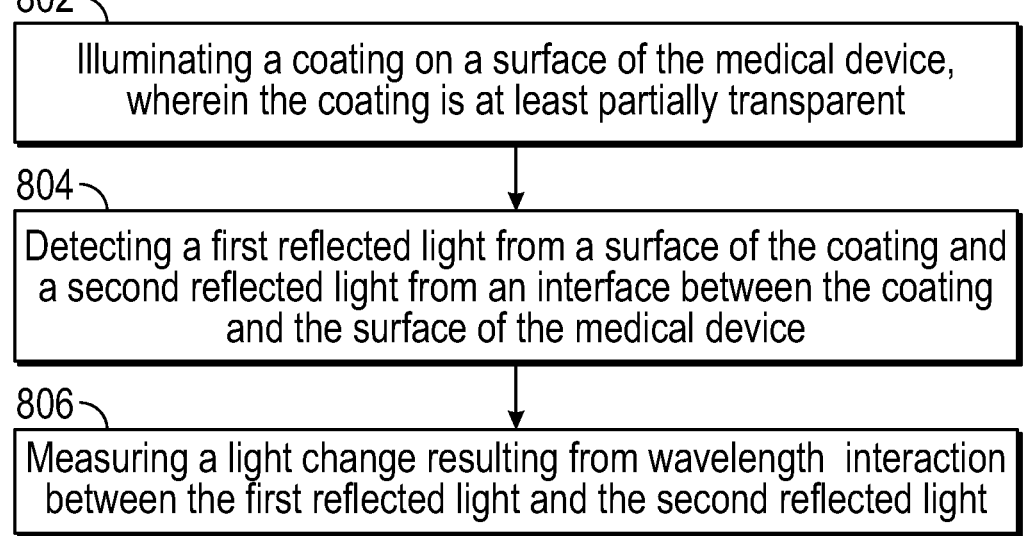
FIG. 8 shows a flow diagram of an example method of inspecting a coating, in accordance with various aspects.

FIG. 8 shows a flow diagram of an example method of inspecting a coating as discussed in examples above and shown illustrated in FIG. 8. In operation 802, a coating on a surface of the medical device is illuminated, wherein the coating is at least partially transparent. In operation 804, a first reflected light from a surface of the coating, and a second reflected light from an interface between the coating and the surface of the medical device are detected. In operation 806, a light change is measured resulting from wavelength interaction between the first reflected light and the second reflected light.

In one example, measuring a light change resulting from wavelength interaction indicates a presence or absence of a coating. Very thin transparent coatings can be difficult to detect. Inspection methods as described may be used to indicate whether a coating was deposited at all, and if any regions were missed. In one example, an absence of a light change indicates an absence of a coating. Detection of an absence of a coating may be useful to determine if a coating procedure was performed at all, or if an applied coating is spotty, or only partially applied. One advantage of methods and devices for inspection as described includes the non-contact nature of the inspection. Risk of damaging the coating is minimal due to the lack of contact.

In one example, measuring a light change resulting from wavelength interaction further includes quantifying a thickness of the coating where the quantification is derived from the light change. In one example, deposited coatings are self-limiting, and a coating thickness is generally uniform across a surface. In another example, measuring a light change resulting from wavelength interaction further includes quantifying variations in thickness of the coating derived from the light change. In non-self-limiting examples, it may be useful to measure how consistent a coating thickness is, in order to adjust a process parameter to make a coating more uniform if desired.

In one example, the light detector 712 includes a spectrometer. In color detection examples as described above, it may be useful to measure small variations in color in a quantifiable and repeatable way. In one example, the spectrometer is an areal spectrometer, that facilitates a surface map indicating thickness variations as described above.

Although methods and devices described are useful for any number of coating materials, one particular area of use includes hydrophobic coatings and/or ultrahydrophobic coatings. These coatings may be very thin, and difficult to inspect without methods and devices as described. In one example, the term hydrophobic physical structure discussed below is in contrast to a chemical coating, lubricant, or other hydrophobic layer whose principal of operation is based on chemistry. In one example, hydrophobic physical structures include nanoscale structures that provide hydrophobicity as described in more detail below.

Figure 9:
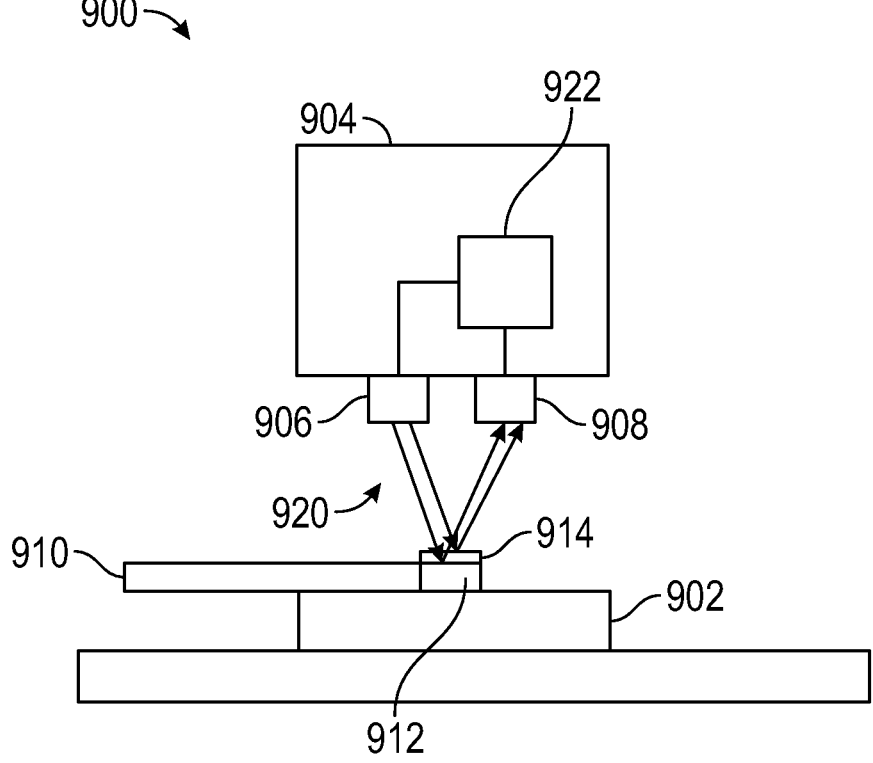
FIG. 9 shows an example of a medical coating inspection device, in accordance with various aspects.

FIG. 9 shows an example of a medical coating inspection device 900. The medical coating inspection device includes a holding fixture 902 configured to hold a medical device for inspection. An example of a medical device 910 is shown for illustration. In the example of FIG. 9, the medical device 910 includes an end portion 912 with a coating 912 being inspected as described in examples above.

The medical coating inspection device 900 further includes a light source 906 and a reflected light detector 908. A device housing 904 is shown in block diagram format. An actual device housing 904 need not be rectangular. The device housing 904 includes measurement analysis circuitry 922. The measurement analysis circuitry 922 is configured to measure a light change resulting from wavelength interaction between a first reflected light from a surface of a coating 914 on the medical device 912 and a second reflected light from an interface between the coating 914 and the surface of the medical device 912. The first reflected light and the second reflected light are indicated generally as light rays 920. In one example, the light rays 920 interact similar to the described process of FIG. 9 above.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Exemplary Aspects

The following exemplary aspects are provided, the numbering of which is not to be construed as designating levels of importance:

Aspect 1 provides a medical device comprising:
a substrate; and
a substantially transparent or translucent anti-stick coating disposed on a surface of the substrate, the anti-stick coating comprising one or more fluorophores internally distributed in the anti-stick coating.

Aspect 2 provides the medical device of Aspect 1, wherein the anti-stick coating is a superhydrophobic coating, a superoleophobic coating, or both.

Aspect 3 provides the medical device of any one of Aspects 1 or 2, wherein the medical device comprises an electrocauterization device, an ultrasonic emitting device, a laser device, or an electrosurgical vessel sealing device.

Aspect 4 provides the medical device of any one of Aspects 1-3, wherein the substrate comprises a jaw, a pair of jaws, a pair of forceps, a prong, or a combination thereof.

Aspect 5 provides the medical device of Aspect 4, wherein the jaw comprises an electrically conductive tissue sealing plate configured to operably couple to a source of electrosurgical energy for treating tissue, and the anti-stick coating is disposed on the electrically conductive tissue sealing plate.

Aspect 6 provides the medical device of any one of Aspects 1-5, wherein the substrate comprises an undulating profile comprising peaks and valleys, wherein the peaks, valleys, or a combination thereof, comprises the anti-stick coating applied thereto.

Aspect 7 provides the medical device of any one of Aspects 1-6, wherein anti-stick coating comprises a visual indicium.

Aspect 8 provides the medical device of Aspect 7, wherein the visual indicium is disposed over at least a portion of the substrate covered by the coating.

Aspect 9 provides the medical device of any one of Aspects 7 or 8, wherein the visual indicium comprises a word, a number, a pattern, a picture, a color, or a combination thereof.

Aspect 10 provides the medical device of Aspect 9, wherein the visual indicium comprises a pigment.

Aspect 11 provides the medical device of any one of Aspects 1-10, wherein the substrate comprises a haptic feature.

Aspect 12 provides the medical device of Aspect 11, wherein the anti-stick coating is disposed over the haptic feature.

Aspect 13 provides the medical device of any one of Aspects 1-12, wherein the substrate comprises a metal, a plastic, a ceramic, a glass, or a combination thereof.

Aspect 14 provides the medical device of Aspect 13, wherein the metal comprises iron, stainless steel, titanium, tantalum, platinum, iridium, tungsten, copper, nickel, gold, aluminum, steel an alloy thereof, or a mixture thereof.

Aspect 15 provides the medical device of any one of Aspects 13 or 14, wherein the plastic material comprises a thermoplastic polymer, a thermoset polymer, or a mixture thereof.

Aspect 16 provides the medical device of any one of Aspects 13-15, wherein the plastic material comprises a polyamide, a polycarbonate, a polyolefin, a polyester, a polyurethane, an epoxy, a copolymer thereof, or a mixture thereof.

Aspect 17 provides the medical device of any one of Aspects 13-16, wherein the plastic material comprises polytetrafluoroethylene, a styrene-butadiene copolymer, ethylene tetrafluoroethylene, a polyvinyl chloride, polyether urethane, a phenol formaldehyde polymer, or a mixture thereof.

Aspect 18 provides the medical device of any one of Aspects 13-17, wherein the ceramic comprises yttria $(Y_2O_3)$, magnesia (MgO), aluminum oxide $(Al_2O_3)$, a magnesium aluminum oxide $(MgAl_2O_4)$, a carbide, an oxycarbide, a nitride, an oxynitride, a boride, an oxyboride, a sulfide, a selenide, a sulfo-selenide, silica, zirconia, silicon-carbide, silicon-nitride, aluminum nitride, or a mixture thereof.

Aspect 19 provides the medical device of any one of Aspects 13-18, wherein the glass comprises soda lime silicate glass, alkali aluminosilicate glass, alkali containing borosilicate glass, alkali aluminophosphosilicate glass, alkali aluminoborosilicate glass, or a mixture thereof.

Aspect 20 provides the medical device of any one of Aspects 1-19, wherein the anti-stick coating comprises a metal, a polymeric material, a ceramic, a glass, or a combination thereof.

Aspect 21 provides the medical device of Aspect 20, wherein the anti-stick coating comprises tungsten disulfide, hexamethyldisiloxane, tetramethyldisiloxane, fluorosilane, a polydimethylsiloxane, a glass, a perfluoropolyether, manganese oxide polystyrene, zinc oxide polystyrene, calcium carbonate, polytetrafluoroethylene, or a mixture thereof.

Aspect 22 provides the medical device of any one of Aspects 1-21, wherein the anti-stick coating comprises a microstructure, a nanostructure, or a combination thereof.

Aspect 23 provides the medical device of Aspect 22, wherein the microstructure comprises a plurality of structural features independently having a major dimension in a range of from about 1 μm to about 1000 μm.

Aspect 24 provides the medical device of any one of Aspects 22 or 23, wherein the microstructure comprises a plurality of structural features independently having a major dimension in a range of from about 250 μm to about 750 μm.

Aspect 25 provides the medical device of any one of Aspects 22-24, wherein the nanostructure comprises a plurality of structural features independently having a major dimension in a range of from about 1 nm to about 100 nm.

Aspect 26 provides the medical device of any one of Aspects 22-25, wherein the nanostructure comprises a plurality of structural features independently having a major dimension in a range of from about 10 nm to about 70 nm.

Aspect 27 provides the medical device of any one of Aspects 22-26, wherein the anti-stick coating comprises a plurality of structural microfeatures and a plurality of structural nanofeatures.

Aspect 28 provides the medical device of Aspect 27, wherein the plurality of nanostructures extend from the plurality of microstructures and are a substrate to the plurality of nanostructures.

Aspect 29 provides the medical device of any one of Aspects 22-28, wherein the microstructure comprises a microwire, a microrod, a microtube, a microsphere, or a microdroplet.

Aspect 30 provides the medical device of any one of Aspects 22-29, wherein the nanostructure comprises a nanowire, a nanorod, a nanotube, a nanosphere, or a nanodroplet.

Aspect 31 provides the medical device of any one of Aspects 22-30, wherein a pitch between adjacent structural features is substantially constant across the medical device.

Aspect 32 provides the medical device of any one of Aspects 22-31, wherein a pitch between adjacent structural features is variable across the medical device.

Aspect 33 provides the medical device of any one of Aspects 22-32, wherein a pitch between adjacent structural features of a first plurality of structural features is constant and a pitch between adjacent structural features of a second plurality of structural features is variable.

Aspect 34 provides the medical device of any one of Aspects 22-33, wherein the microstructure, nanostructure, or a mixture thereof comprise the anti-stick coating.

Aspect 35 provides the medical device of any one of Aspects 1-34, wherein a thickness of the anti-stick coating is in a range of from about 0.1 nm to about 90 nm.

Aspect 36 provides the medical device of any one of Aspects 1-35, where a thickness of the anti-stick coating is in a range of from about 0.1 nm to about 15 nm.

Aspect 37 provides the medical device of Aspect 36, where a thickness of the anti-stick coating is in a range of from about 5 nm to about 10 nm.

Aspect 38 provides the medical device of any one of Aspects 36 or 37, wherein the thickness of the anti-stick coating is substantially constant across the medical device.

Aspect 39 provides the medical device of any one of Aspects 36 or 38, wherein the thickness of the anti-stick coating is variable across the medical device.

Aspect 40 provides the medical device of any one of Aspects 1-39, wherein the anti-stick coating is a continuous coating.

Aspect 41 provides the medical device of any one of Aspects 1-40, wherein the anti-stick coating is a discontinuous coating.

Aspect 42 provides the medical device of Aspect 41, wherein the anti-stick coating is discontinuous and comprises a first anti-stick coating and a second anti-stick coating.

Aspect 43 provides the medical device of Aspect 42, wherein the first anti-stick coating and the second anti-stick coating comprise the same material, structure, or combination thereof.

Aspect 44 provides the medical device of any one of Aspects 1-43, further comprising an adhesive layer between the substrate and the anti-stick coating.

Aspect 45 provides the medical device of Aspect 44, wherein the adhesive layer comprises a pressure-sensitive adhesive.

Aspect 46 provides the medical device of any one of Aspects 1-45, wherein the anti-stick coating is a first anti-stick coating and the medical device further comprises a second anti-stick coating adjacent to the first anti-stick coating.

Aspect 47 provides the medical device of any one of Aspects 1-46, wherein a contact angle of the medical device is at least 120 degrees, as determined using ASTM D7334-08.

Aspect 48 provides the medical device of any one of Aspects 1-47, wherein a contact angle of the medical device is at least 150 degrees, as determined using ASTM D7334-08, as determined using ASTM D7334-08.

Aspect 49 provides the medical device of any one of Aspects 1-48, wherein a contact angle of the anti-stick coating is in a range of from about 120 degrees to about 180 degrees, as determined using ASTM D7334-08.

Aspect 50 provides the medical device of any one of Aspects 1-49, wherein a contact angle of the anti-stick coating is in a range of from about 140 degrees to about 160 degrees, as determined using ASTM D7334-08.

Aspect 51 provides the medical device of any one of Aspects 1-50, wherein the substrate is flexible.

Aspect 52 provides the medical device of any one of Aspects 1-51, wherein the anti-stick coating, the substrate, or both are transparent.

Aspect 53 provides the medical device of any one of Aspects 1-52, wherein the one more fluorophores are present at less than about 10 wt % of the anti-stick coating.

Aspect 54 provides the medical device of any one of Aspects 1-53, wherein the one more fluorophores are present at less than about 5 wt % of the anti-stick coating.

Aspect 55 provides the medical device of any one of Aspects 1-54, wherein the one more fluorophores are present in a range of from about 0.1 wt % to about 10 wt % of the anti-stick coating.

Aspect 56 provides the medical device of any one of Aspects 1-55, wherein the one more fluorophores are present in a range of from about 2 wt % to about 4 wt % of the anti-stick coating.

Aspect 57 provides the medical device of any one of Aspects 1-56, wherein the one or more fluorophores are homogenously distributed about the anti-stick coating.

Aspect 58 provides the medical device of any one of Aspects 1-57, wherein the one or more fluorophores are heterogeneously distributed about the anti-stick coating.

Aspect 59 provides the medical device of any one of Aspects 1-58, wherein the one or more fluorophores comprise the same fluorophore.

Aspect 60 provides the medical device of any one of Aspects 1-59, wherein the one or more fluorophores comprise different fluorophores.

Aspect 61 provides the medical device of any one of Aspects 1-60, wherein the one or more fluorophores are biocompatible.

Aspect 62 provides the medical device of any one of Aspects 1-61, wherein the one or more fluorophores comprise an organic non-protein fluorophore, an organic dye, a nucleic acid dye, a fluorescent protein, or a mixture thereof.

Aspect 63 provides the medical device of Aspect 62, wherein the organic non-protein fluorophore comprises xanthene, cyanine, squaranine, squarine rotaxane, naphthalene, coumarin, oxadiazole, anthracene, pyrene, oxazine, acridine, arylmethine, tetrapyrrole, dipyrromethene, a derivative of any one of the preceding, or a mixture thereof.

Aspect 64 provides the medical device of any one of Aspects 62 or 63, wherein the organic dye comprises hydroxycoumarin, aminocoumarine, methoxycoumarine, allophycocyanin, or a mixture thereof.

Aspect 65 provides the medical device of any one of Aspects 62-64, wherein the nucleic acid dye comprises 4',6-diamidino-2-phenylindole, plicamycin, toyomycin, ethidium bromide, propidium iodide, or a combination thereof.

Aspect 66 provides the medical device of any one of Aspects 1-65, wherein the fluorescent protein comprises a green fluorescent protein.

Aspect 67 provides the medical device of any one of Aspects 22-66, wherein the microstructure and the nanostructure each comprise a different fluorophore.

Aspect 68 provides the medical device of Aspect 67, wherein the different fluorophores emit electromagnetic radiation having different wavelengths.

Aspect 69 provides a method of making the medical device of any one of Aspects 1-68, the method comprising disposing the anti-stick coating on at least a portion of the substrate.

Aspect 70 provides the method of Aspect 69, wherein the disposing comprises a sol-gel coating process, a cold spray coating process, chemical vapor deposition, physical vapor deposition, thermal spray deposition, an in situ polymerization, spin-coating, dip-coating, an electrodeposition, additive manufacturing, or a combination thereof.

Aspect 71 provides the method of any one of Aspects 69 or 70, further comprising molding, imprinting, etching, or a combination thereof, to impart the structural microstructure feature, structural nanostructure feature, or a combination thereof.

Aspect 72 provides the method of any one of Aspects 69-71, further comprising mixing the one or more fluorophores with the anti-stick coating prior to disposing the anti-stick coating on the substrate.

Aspect 73 provides the method of any one of Aspects 69-72, wherein disposing the anti-stick coating on at least a portion of the substrate comprises applying a coating composition to the portion of the substrate Aspect 74 provides the method of Aspect 72, further comprising including a first fluorophore at a first location of the anti-stick coating and including a second fluorophore, different from the first fluorophore, at a second location of the anti-stick coating.

Aspect 75 provides the method of Aspect 74, wherein the first location and the second location are vertically arranged with respect to each other, with respect to a major surface of the substrate.

Aspect 76 provides the method of Aspect 74, wherein the first location and the second location are horizontally arranged with respect to each other, with respect to a major surface of the substrate.

Aspect 77 provides a method of inspecting the medical device of any one of Aspects 1-76, the method comprising:

contacting at least a portion of the medical device with electromagnetic radiation; and measuring a fluorescent emission from the medical device.

Aspect 78 provides the method of Aspect 77, further comprising correlating a non-zero amount of fluorescent emission with presence of the anti-stick coating.

Aspect 79 provides the method of any one of Aspects 77 or 78, further comprising mapping the location of the anti-stick coating based on the measured fluorescent emission.

Aspect 80 provides the method of any one of Aspects 77-79, further comprising determining a thickness of the anti-stick coating based on the measured fluorescent emission.

Aspect 81 provides a method for inspecting a coating on a medical device comprising:

illuminating a coating on a surface of the medical device, wherein the coating is at least partially transparent;

detecting a first reflected light from a surface of the coating and a second reflected light from an interface between the coating and the surface of the medical device; and measuring a light change resulting from wavelength interaction between the first reflected light and the second reflected light.

Aspect 82 provides the method for inspecting a coating on a medical device of Aspect 81, wherein measuring a light change includes measuring constructive interference.

Aspect 83 provides the method for inspecting a coating on a medical device of any one of Aspects 81 or 82, wherein measuring a light change includes measuring destructive interference.

Aspect 84 provides the method for inspecting a coating on a medical device of any one of Aspects 81-83, wherein measuring a light change includes measuring a color change.

Aspect 85 provides the method for inspecting a coating on a medical device of any one of Aspects 81-84, wherein illuminating a coating includes illuminating with polychromatic light.

Aspect 86 provides the method for inspecting a coating on a medical device of any one of Aspects 81-85, wherein illuminating a coating includes illuminating with monochromatic light.

Aspect 87 provides the method for inspecting a coating on a medical device of any one of Aspects 81-86, further including quantifying a thickness of the coating derived from the light change.

Aspect 88 provides the method for inspecting a coating on a medical device of any one of Aspects 81-87, further including quantifying variations in thickness of the coating derived from the light change.

Aspect 89 provides a method of manufacturing a coated medical device comprising:

forming a coating on a surface of the medical device wherein the coating includes a hydrophobic physical structure on a surface of the coating, wherein the coating is at least partially transparent;

illuminating the coating;

detecting a first reflected light from the surface of the coating and a second reflected light from an interface between the coating and the surface of the medical device; and measuring a light change resulting from wavelength interaction between the first reflected light and the second reflected light.

Aspect 90 provides the method of manufacturing a coated medical device of Aspect 89, wherein the coating includes polysiloxane.

Aspect 91 provides the method of manufacturing a coated medical device of any one of Aspects 89 or 90, wherein the coating includes hexamethyldisiloxane (HMDSO).

Aspect 92 provides the method of manufacturing a coated medical device of any one of Aspects 89-91, wherein the coating includes fluorosilane.

Aspect 93 provides the method of manufacturing a coated medical device of any one of Aspects 89-92, wherein forming a coating includes chemical vapor deposition (CVD).

Aspect 94 provides the method of manufacturing a coated medical device of any one of Aspects 89-93, wherein forming a coating includes physical vapor deposition (PVD).

Aspect 95 provides the method of manufacturing a coated medical device of any one of Aspects 89-94, wherein forming the coating including modifying a surface of the coating after deposition to form the hydrophobic physical structure.

Aspect 96 provides the method of manufacturing a coated medical device of Aspect 95, wherein modifying the surface of the coating includes etching the coating.

Aspect 97 provides a medical coating inspection device, comprising:

a holding fixture configured to hold a medical device for inspection;

a light source;

a reflected light detector; and measurement analysis circuitry configured to measure a light change resulting from wavelength interaction between a first reflected light from a surface of a coating on the medical device and a second reflected light from an interface between the coating and the surface of the medical device.

Aspect 98 provides the medical coating inspection device of Aspect 97, wherein the reflected light detector includes a spectrometer.

Aspect 99 provides the medical coating inspection device of any one of Aspects 97 or 98, wherein the light source includes polychromatic light.

Aspect 100 provides the medical coating inspection device of any one of Aspects 97-99, wherein the light source includes monochromatic light.

Aspect 101 provides the medical coating inspection device of any one of Aspects 97-100, wherein the light source includes ultraviolet wavelength light.

Aspect 102 provides a method for inspecting a coating on a medical device comprising:

illuminating a surface of the medical device;

in regions of the surface where a coating is present, detecting a first reflected light from a surface of a coating and a second reflected light from an interface between the coating and the surface of the medical device;

measuring a light change resulting from wavelength interaction between the first reflected light and the second reflected light; and in regions of the surface where a coating is absent, detecting an absence of a light change.

What is claimed is:

1. A medical device comprising:
   a substrate; and
   a substantially transparent or translucent anti-stick coating disposed on a surface of the substrate, the anti-stick coating comprising one or more fluorophores internally distributed in the anti-stick coating, wherein
   a thickness of the anti-stick coating ranges from about 10 nanometers to about 300 nanometers.

2. The medical device of claim 1, wherein the anti-stick coating is a superhydrophobic coating, a superoleophobic coating, or both.

3. The medical device of claim 1, wherein the medical device comprises an electrocauterization device, an ultrasonic emitting device, a laser device, or an electrosurgical vessel sealing device.

4. The medical device of claim 1, wherein the substrate comprises a jaw, a pair of jaws, a pair of forceps, a prong, or a combination thereof.

5. The medical device of claim 4, wherein the jaw comprises an electrically conductive tissue sealing plate configured to operably couple to a source of electrosurgical energy for treating tissue, and the anti-stick coating is disposed on the electrically conductive tissue sealing plate.

6. The medical device of claim 1, wherein the substrate comprises a metal, a plastic, a ceramic, a glass, or a combination thereof.

7. The medical device of claim 6, wherein the metal comprises iron, stainless steel, titanium, tantalum, platinum, iridium, tungsten, copper, nickel, gold, aluminum, steel an alloy thereof, or a mixture thereof.

8. The medical device of claim 6, wherein the plastic comprises a thermoplastic polymer, a thermoset polymer, or a mixture thereof.

9. The medical device of claim 1, wherein the anti-stick coating comprises a metal, a polymeric material, a ceramic, a glass, or a combination thereof.

10. The medical device of claim 9, wherein the anti-stick coating comprises tungsten disulfide, hexamethyldisiloxane, tetramethyldisiloxane, fluorosilane, a polydimethylsiloxane, a glass, a perfluoropolyether, manganese oxide polystyrene, zinc oxide polystyrene, calcium carbonate, polytetrafluoro-ethylene, or a mixture thereof.

11. The medical device of claim 1, wherein the anti-stick coating comprises a microstructure, a nanostructure, or a combination thereof.

12. The medical device of claim 11, wherein the microstructure comprises a plurality of structural features independently having a major dimension in a range of from about 1 μm to about 1000 μm.

13. The medical device of claim 11, wherein the nanostructure comprises a plurality of structural features independently having a major dimension in a range of from about 1 nm to about 100 nm.

14. The medical device of claim 11, wherein the anti-stick coating comprises a plurality of structural microfeatures and a plurality of structural nanofeatures.

15. The medical device of claim 1, wherein a contact angle of the anti-stick coating is in a range of from about 120 degrees to about 180 degrees, as determined using ASTM D7334-08.

16. The medical device of claim 1, wherein the one more fluorophores are present at less than about 10 wt % of the anti-stick coating.

17. The medical device of claim 1, wherein the one or more fluorophores are biocompatible.

18. The medical device of claim 1, wherein the one or more fluorophores comprise an organic non-protein fluoro-phore, an organic dye, a nucleic acid dye, a fluorescent protein, or a mixture thereof.

19. A method of making the medical device of claim 1, the method comprising disposing the anti-stick coating on at least a portion of the substrate.

20. A method of inspecting the medical device of claim 1, the method comprising:

contacting at least a portion of the medical device with electromagnetic radiation; and measuring a fluorescent emission from the medical device.

* * * * *